United States Patent [19]

Johns et al.

[11] 4,067,227

[45] Jan. 10, 1978

[54] HYDROGEN TRANSFER SYSTEM FOR GAS CHROMATOGRAPH

[75] Inventors: Theron Johns, Orange; Edward A. Berry, Anaheim, both of Calif.

[73] Assignee: Carle Instruments, Inc., Fullerton, Calif.

[21] Appl. No.: 559,807

[22] Filed: Mar. 19, 1975

[51] Int. Cl.[2] ............................................. G01N 31/08
[52] U.S. Cl. .................................................... 73/23.1
[58] Field of Search ...................... 73/23.1, 23, 19; 55/158; 23/232 C, 232 R, 254 R

[56] References Cited

U.S. PATENT DOCUMENTS

| | | | |
|---|---|---|---|
| 3,408,854 | 11/1968 | Larson | 73/23.1 |
| 3,438,241 | 4/1969 | McKinley | 73/19 |
| 3,494,174 | 2/1970 | Green et al. | 73/23.1 |
| 3,585,002 | 6/1971 | Boys | 73/23.1 |
| 3,638,397 | 2/1972 | Charlton | 73/23.1 X |

*Primary Examiner*—Richard C. Queisser
*Assistant Examiner*—Stephen A. Kreitman
*Attorney, Agent, or Firm*—Knobbe, Martens, Olson, Hubbard & Bear

[57] ABSTRACT

A gas chromatograph and chromatographic process for determining hydrogen in a sample in which the hydrogen is passed from one carrier through a selectively permeable barrier into a carrier gas having low thermal conductivity.

10 Claims, 7 Drawing Figures

HYDROGEN TRANSFER SYSTEM FOR GAS CHROMATOGRAPH

This invention relates to analytical methods and means for the quantitative determination of hydrogen in a sample by transferring the hydrogen constituent from a first stream to a second stream. In the preferred embodiment, the quantitative method employed is gas chromatography, but other analytical means and methods may be employed in the practice of the use of this invention. The transfer depends on the differential pressure of hydrogen across a membrane selected and operated in a way to make the membrane permeable only to hydrogen. A common membrane material for the practice of this form of the invention is palladium metal and its alloys with other metals, but any other membrane material permeable to hydrogen could be used in the practice of the invention. Further, other gases and classes of membranes can be combined to practice this invention in a way similar to that described for hydrogen.

In general, the gas chromatographic analytical method is widely used and well known for quantitative analysis of gases and vapors. The technique of gas chromatography comprises injecting a sample, which may include several constituents, into a carrier gas stream. Helium is one commonly used carrier gas but many other gases may be used in a similar way. After the sample has been injected in the carrier gas stream it is carried to a chromatographic column, a tubular member having a packing which has different affinity for the several components of the sample. The constituents of the sample, therefore, move at different rates and, consequently, the sample is separated into its several constituents. A detector connected to the exit end of the column quantitatively measures the amount of each constituent in the carrier gas as the gas emerges from the end of the column. Detectors of many types are used, but the most commonly used type of detector is the thermal conductivity detector. Thermal conductivity detectors as are commonly used in gas chromatography utilize one or more heated sensing elements to measure the thermal conductivity of the gas which is in contact with the sensor as the gas emerges from the column. Thus, change in measured thermal conductivity is proportional to the amount of sample constituent present.

Sensors are usually metal filaments or thermistors, elements that have a predictable change in resistance in proportion to the change in temperature of the sensor. Normally sensors are carefully matched as pairs and are arranged in a Wheatstone bridge circuit enabling one of the sensors to sense the emerging gas from the chromatographic column and the second sensor to serve as a reference in the Wheatstone bridge by passing pure carrier gas over said reference sensor. One form of this invention utilizes a special thermal conductivity detector which has sensing elements having significantly different resistances before the sensors are heated. In this form of the invention two different carrier gases are used and the sensors are heated and balanced such that in operation the resistance of the two elements become equal and a balanced Wheatstone bridge is achieved, even though two different gases are flowing each past the two sensors in their respective flow chambers. In another form of this invention it is alternately possible to use two thermal conductivity detectors and two Wheatstone bridges, both of more conventional type. In this form one detector and bridge is operated on one carrier gas and the second detector and bridge is operated on a second carrier gas of a different type. The practice of the use of this invention is, however, not limited to thermal conductivity detectors and other detectors may also be used.

Although gas chromatography is the analytical method normally utilized, it will be seen later that some forms of the invention do not require that gas chromatography be used. The essential feature in all forms of the invention is that a means is provided whereby hydrogen is transferred from a first stream to a second stream for analytical measurement.

The means of transfer is by differential pressure across a membrane which is permeable only to the constituent or constituents which are advantageously measured by transfer. In the specific case of hydrogen, selective diffusion or permeation by any means through platinum and palladium and alloys of these metals is well known. However, the transfer of hydrogen from a first stream across a membrane made of these materials to a second stream for analytical measurement and the construction and operation of a system for the analytical measurement is not taught in the art.

A principal feature of this invention is a method and an apparatus for determining hydrogen quantitatively with high sensitivity and high accuracy. By a quantitative determination, as the term is used in this specification, we mean a determination which gives an output signal which is proportionally related to the quantity of hydrogen present in the sample.

Another important feature of this invention is to provide a system for quantitative gas chromatographic detection of hydrogen and other components of a sample mixture in a single analysis such that the sensitivities for all components, including hydrogen, are similar and high in a relative sense.

Another feature in this invention is to eliminate the complication of peak reversal or "W" configuration previously experienced whenever hydrogen is the sample or part of the sample in analyses that utilize helium as the carrier gas.

Another feature of this invention is the achievement of a chromatographic or other analytical instrument system in which hydrogen may be determined in single samples as a peak of the same polarity as other sample components, for example, oxygen, nitrogen hydrocarbons, etc., when helium is used as a carrier gas.

Another important feature and the means by which the desired results of the invention are accomplished constitutes a hydrogen transfer system for transferring hydrogen through a membrane which is selectively permeable to hydrogen from a first carrier gas stream into a second carrier gas stream in which hydrogen can be determined with high precision and sensitivity.

The system which is the subject of this invention quantitatively determines hydrogen in a sample and includes means for injecting a sample, which includes hydrogen as a constituent, into a first carrier gas stream, means for separating the constituents of the sample from each other in the first carrier gas stream, means for transferring the hydrogen constituent of the sample selectively from the first carrier gas stream to the second carrier gas stream, and means for detecting hydrogen quantitatively in a second gas stream.

In one form of the invention, the aforementioned separating means may be eliminated in the case of gas mixtures wherein only hydrogen need be measured and the other components are not reactive with the hydrogen component in the transfer tube.

As a gas chromatograph, the apparatus comprises helium or other gas of high thermal conductivity as a carrier gas system, and nitrogen or other gas of relatively lower thermal conductivity, e.g., argon, etc., as a second carrier gas system, means for injecting a sample which includes hydrogen as a sample constituent into the helium carrier gas system, a chromatographic column in the helium carrier gas system for separating hydrogen from the other sample constituents, means for transferring the hydrogen constituent from the helium carrier gas system to the nitrogen carrier gas system without transferring other sample constituents and means in the nitrogen carrier gas system for detecting the hydrogen constituent of the sample. The chromatograph typically also includes means for detecting sample constituents in the helium carrier gas system.

Another feature of the invention is the provision of a detecting system in which a Wheatstone bridge type detector is balanced with two carrier gases, for example helium and nitrogen, with the hydrogen being detected in the nitrogen carrier gas and all other constituents being detected in the helium carrier gas, the output of the detector giving a series of spaced, symmetrical, chromatographic tracing peaks all in the same direction and of the same output electrical polarity.

These and other advantages, features and characteristics of the invention will be more apparent from the following discussion and from the drawings.

The drawings and the descriptions contained herein are merely exemplary of the invention and do not purport to be exhaustive in describing the systems or procedures in which the invention can be utilized and are not limiting with respect to the invention.

Figure 1:
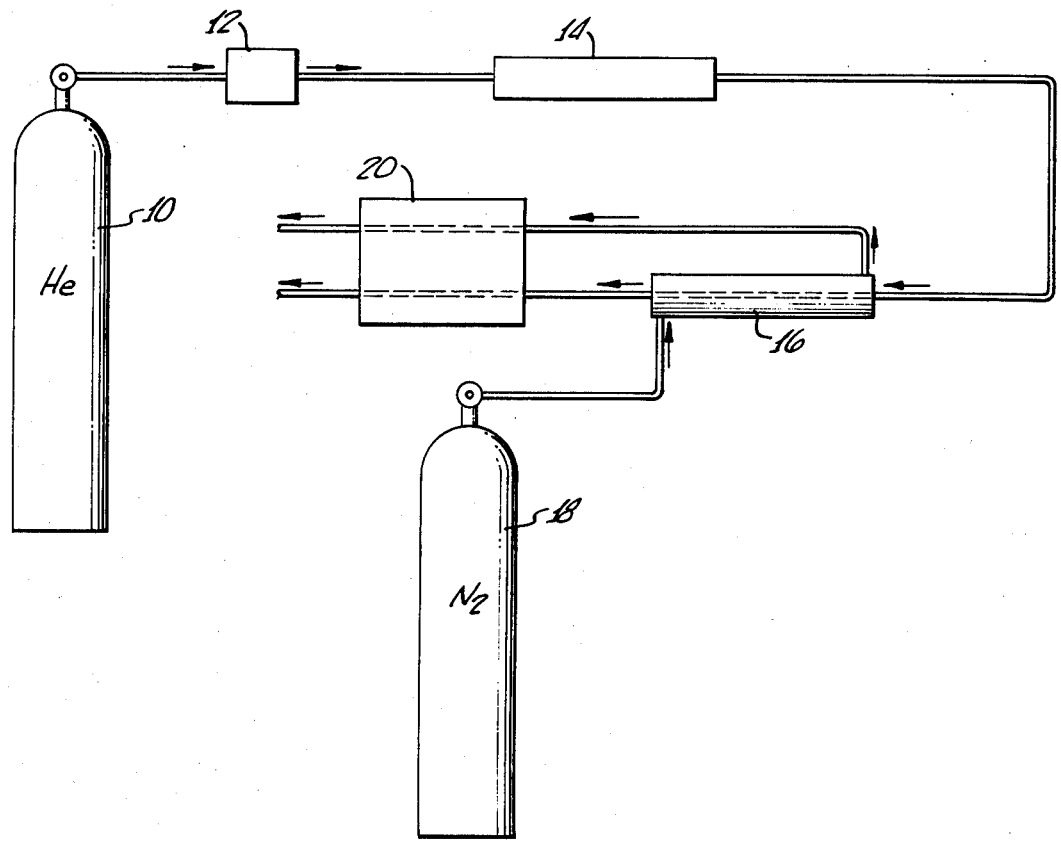
FIG. 1 is a schematic representation of a gas chromatograph utilizing the concept of the present invention.

In the exemplary chromatographic analysis system depicted in FIG. 1, the system includes a first carrier gas system which may, in the exemplary embodiment, be adapted to use helium from a tank indicated at 10. The tank of helium, or other high thermal conductivity carrier gas, is not usually a part of the chromatographic system but is connected to the chromatograph for use. Carrier gas flows from the tank 10 through a sample inlet 12 which may be of any type, such as the well known septum and sample valve types. The carrier gas then flows through the chromatographic column 14 and through the hydrogen transfer system shown generally at 16 to the detector 20. A second carrier gas system for a lower thermal conductivity gas, typically nitrogen or an equivalent, from a bottle 18 flows through a second chamber of the hydrogen transfer system 16 and then to the detector 20.

Figure 2:
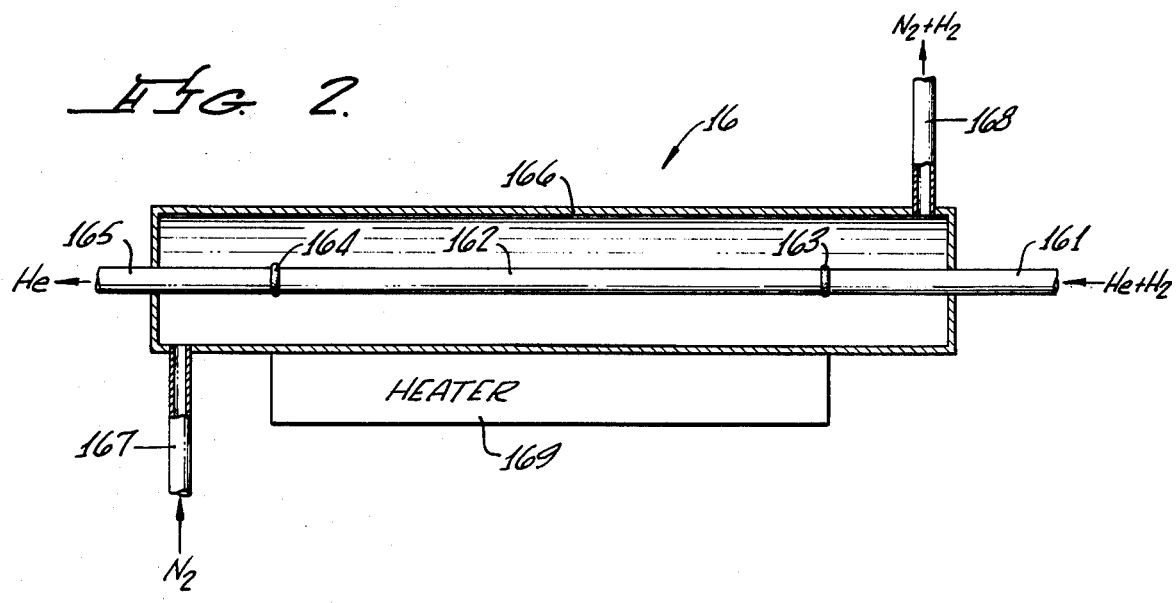
FIG. 2 is a schematic representation of the hydrogen transfer system of the present invention.

The hydrogen transfer system is shown in greater detail in FIG. 2. The first carrier gas flows into the hydrogen transfer system through an input tube 161 and then through a hydrogen transfer tube 162 which is secured at one end by a silver solder or weld bead, or other connector 163, to the input tube 161 and at the other end by a similar weldment or connector 164 to an output tube 165. Typically, the input and output tubes 161 and 165 are constructed of stainless steel or some other metal which is inert to and impermeable to all constituents of the sample and to the carrier gas. The hydrogen transfer tube 162 is made of thin-walled platinum, palladium or an alloy of these metals, the characteristics of which are discussed in greater detail hereinafter, which, at certain temperatures, is permeable to hydrogen alone. This selective permeability of the hydrogen transfer tube to hydrogen permits the hydrogen constituent of the sample to migrate to an outer chamber 166 surrounding the hydrogen transfer tube 162. Nitrogen flows into the outer chamber 166 through an inlet 167 and outwardly through outlet 168. It is important that the nitrogen flow in a direction counter to the flow of the helium, although less efficient operation is possible if both the helium and nitrogen flow in the same direction. The entire assembly is heated by a heater shown generally at 169; however, the only part of the hydrogen transfer system which needs to be heated is the hydrogen transfer tube 162, since the platinum, palladium metals and their alloys are selectively permeable to hydrogen only within certain temperature ranges. The heater may be of the "shell type" in which Nichrome heating coil is mounted in ceramic holding elements and the hydrogen transfer tube is heated by radiation from the inside of the outer chamber 166. Alternatively, a quartz or other nonconductive tube can be used as the outer chamber 166 and the hydrogen transfer tube heated by induction. As another alternative a source of electric power can be applied at or adjacent the two ends of the hydrogen transfer tube to heat the tube by electrical resistance, flowing the current through the hydrogen transfer tube proper. Any type of heating may be used, since the type of heating is usually of small consequence, so long as the proper temperature range is obtained.

In operation, helium is flowing continuously through the chromatographic system, through the sample inlet, the column, the hydrogen transfer tube and one leg of the detector 20. Likewise, nitrogen is flowing continuously through the outer chamber of the hydrogen transfer system 16 and through the other leg of the detector 20. In this steady state, the two legs of the detector, one sensing the helium carrier gas and the other sensing the nitrogen carrier gas, are electronically balanced to give the steady state voltage level which causes the chromatographic recorder to trace a straight line on the margin of the paper.

By using a pair of thermistors or other thermal conductivity sensors of appropriately different resistance for the two thermal conductivities, the detectors balance for these conditions and functions in the same way as a thermal conductivity detector is balanced with a single carrier gas—with one important advantage. There is no need for detector polarity switching during the analysis. Because of the relative differences in the thermal conductivity, the signal polarity from hydrogen in nitrogen is opposite that of oxygen in helium, for example. Many other examples could be cited comparable to the case for oxygen, since only a very few gases have high thermal conductivities, helium and neon for example, and, of course, hydrogen. But opposite polarity signals from opposite sides of the detector result in signals of the same polarity at the recorder. Fine balancing and adjustment is made in the same way as is done in the conventional thermal conductivity detector circuits.

A sample is injected through a rubber septum or using a gas sampling valve. Typically the amount of sample is measured and small in volume and injected as a "plug". In many analyses a typical sample size would be the order of ½ milliliter. In the exemplary embodiment, the sample is injected into the first carrier gas stream. The sample is carried to the head of the chromatographic column 14. As the carrier gas continues to flow through the column, it moves the sample through the column. However, the various constituents of the sample move at different rates, resulting in a net separation of the respective sample constituents. Using molecular sieve type 5A as the column packing, hydrogen is well separated from oxygen and from the other components of a fixed gas sample. Consequently, when the hydrogen reaches the hydrogen transfer system in the first carrier gas, it is spaced from the other constituents. The palladium tube is maintained in an optimum temperature range and the hydrogen diffuses through the palladium membrane from the zone of high hydrogen partial pressure, in the first carrier gas system, to a zone of lower hydrogen partial pressure in the second carrier gas system. The second carrier gas is flowing counter to the direction of the first carrier gas and, therefore, the partial pressure of hydrogen in the second carrier gas adjacent to the membrane will always be lower than the partial pressure of hydrogen in the first carrier gas. The partial pressure of hydrogen in the second carrier gas at the end of the contact zone for the first carrier gas is essentially zero and the net diffusion of hydrogen will always be from the first to the second carrier gas.

Palladium and the platinum are both permeable to hydrogen; however, palladium and certain palladium alloys are the preferred hydrogen permeable barrier alloys. Accordingly, reference is made herein to a palladium barrier with the understanding that platinum and platinum alloys, while less efficient in most instances, are the full equivalent for all purposes and are included within the use of the aforesaid term. Similarly, reference to palladium is made with the understanding that this reference encompasses hydrogen permeable palladium alloys as well as essentially pure palladium.

In the preferred embodiment, the hydrogen permeable barrier is an elongate, thin-walled palladium-silver alloy tube having a wall thickness of about 0.005 inch. The wall thickness and the length of the tube may be varied over a broad range, however, depending upon the concentrations of hydrogen which are to be determined, operating temperature, and other design criteria. In a typical system, the hydrogen permeable barrier tube may be from 4 to 20 inches in length.

The palladium barrier is adequately permeable to hydrogen for some analytical methods at temperatures above 100° to 150° C, depending upon the wall thickness. The best operating temperature, however for the preferred transfer tube used, for maximum sensitivity and linearity for all components, has been found experimentally to be between about 500° C and about 650° C. Within this range, the hydrogen transfer system can handle hydrogen from the low parts-per-million up to 100%. These experiments also confirmed that there is a short but finite time required for the hydrogen to permeate the palladium alloy. Thus, there is a relationship between the transfer tube temperature and the hydrogen concentration which influences sensitivity and linearity. This is because the concentration determines the pressure differential of the hydrogen across the tube wall. This differential acts as the driving force on the hydrogen, and the greater the concentration of hydrogen per unit volume of helium, the greater the pressure differential.

The design of the transfer tube takes advantage of this effect by making the flow of nitrogen counter to the flow of helium, thus ensuring that hydrogen entering the nitrogen flow is immediately swept from the tube and the maximum possible pressure differential is maintained.

Figure 5:
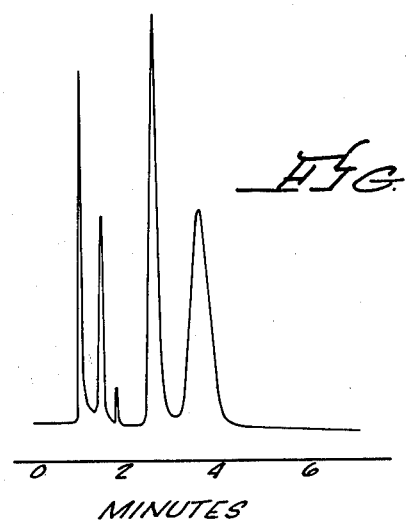
FIG. 5 is a typical chromatograph tracing.

Optimum flow rate for the first carrier gas system, usually helium, is easily determined experimentally for any given system. Generally, the lowest helium flow rate consistent with good column performance and acceptable retention times should be used. The response signal for a sample, when a thermal conductivity detector is used, will increase with a decrease in a flow rate of either the first carrier gas or the second carrier gas or both. The flow rate of the second carrier gas, usually nitrogen, should normally be adjusted to a flow consistent with the volumes of the transfer tube and detector. In the system described below, flow within the range of 30 to 70 ml-min is optimum. This provides reasonable detector response, while maintaining a balancing flow through the detector relative to the flow of the first carrier gas. This ensures a wide range adjustment capability for the recorder zero setting. Peak shape for hydrogen improves with faster flow rate, but some loss in detector response also occurs. The chromatographic trace shown in FIG. 5 is typical of separation and peak shapes which can be obtained using optimum flow and temperature values which are easily determined experimentally.

It will be noted that all of the peaks are in the same direction from the zero or baseline. With helium carrier feeding one side of the thermal conductivity detector and nitrogen feeding the other side of the detector, there would, of course, be a substantial imbalance created by the different thermal conductivity of the two carrier gases. By using a pair of thermistors or filament detectors of appropriately different resistances for the two different thermal conductivities, the hydrogen transfer system detector is balanced for these conditions and functions exactly the same way as a thermal conductivty detector would with a single carrier gas, except that there is no need for detector polarity switching during the analysis.

Figure 3:
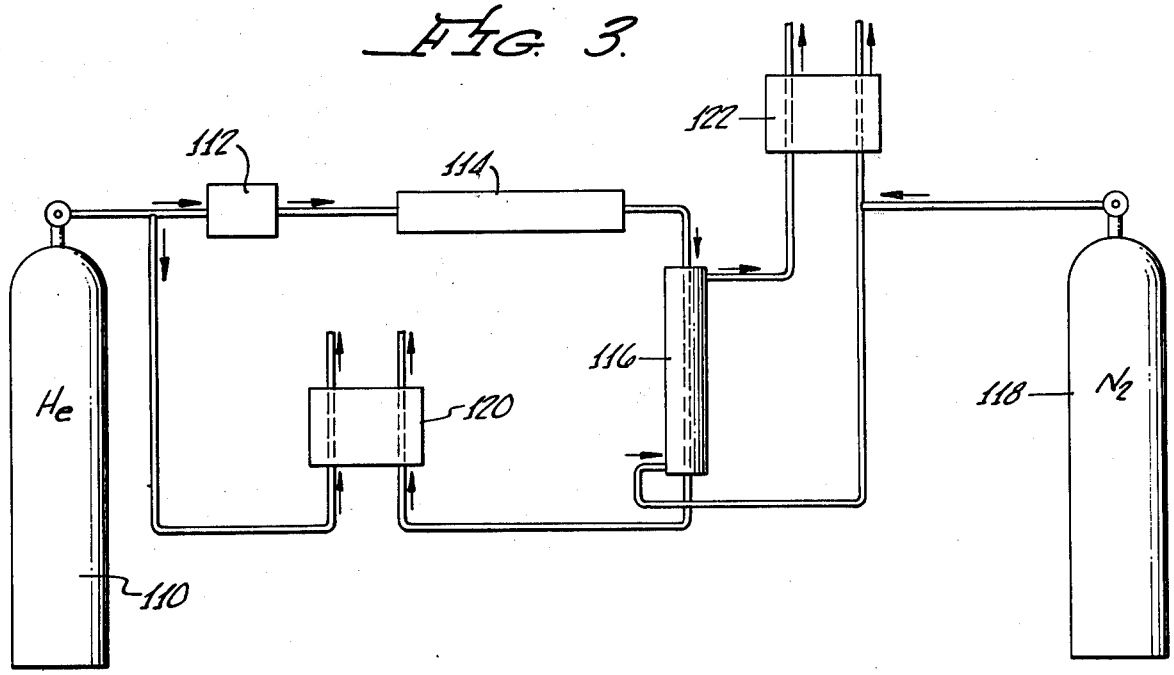
FIG. 3 is a schematic diagram of a gas chromatographic system of an alternative design utilizing the concept of the present invention.

Similar results can be obtained using a system of the type illustrated schematically in FIG. 3 in which helium flows from a source indicated at 110 through a sample inlet 112, a chromatographic column 114 and a hydrogen transfer system 116, as described in respect to FIG. 1. In this embodiment, the helium stream is split and also flows to a helium carrier detector 120 which is balanced on both sides with the same carrier, helium. Nitrogen from a source 118 flows by one path through the hydrogen transfer system 116 to a nitrogen carrier gas balanced detector 122, and by another path directly to the detector. The signals from these two detectors would normally be shown in traces on different recorders, but could be shown on the same chromatographic trace through appropriate electronic switching.

Figure 4A:
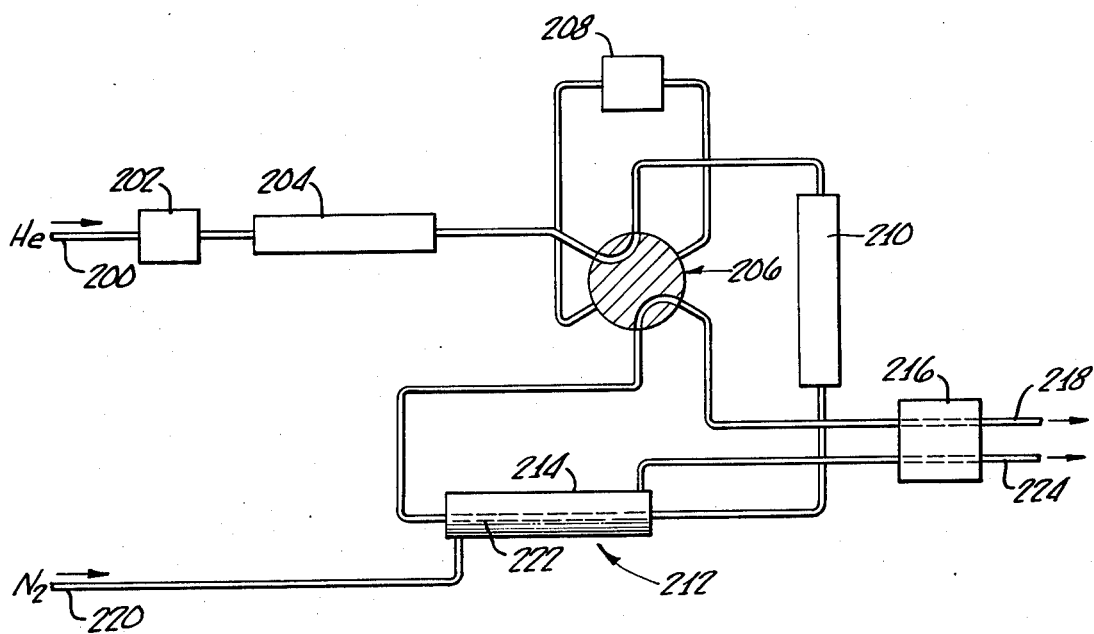
FIGS. 4A and 4B are schematic diagrams of an alternative gas chromatographic system using the present invention in two modes of operation.
Figure 4B:
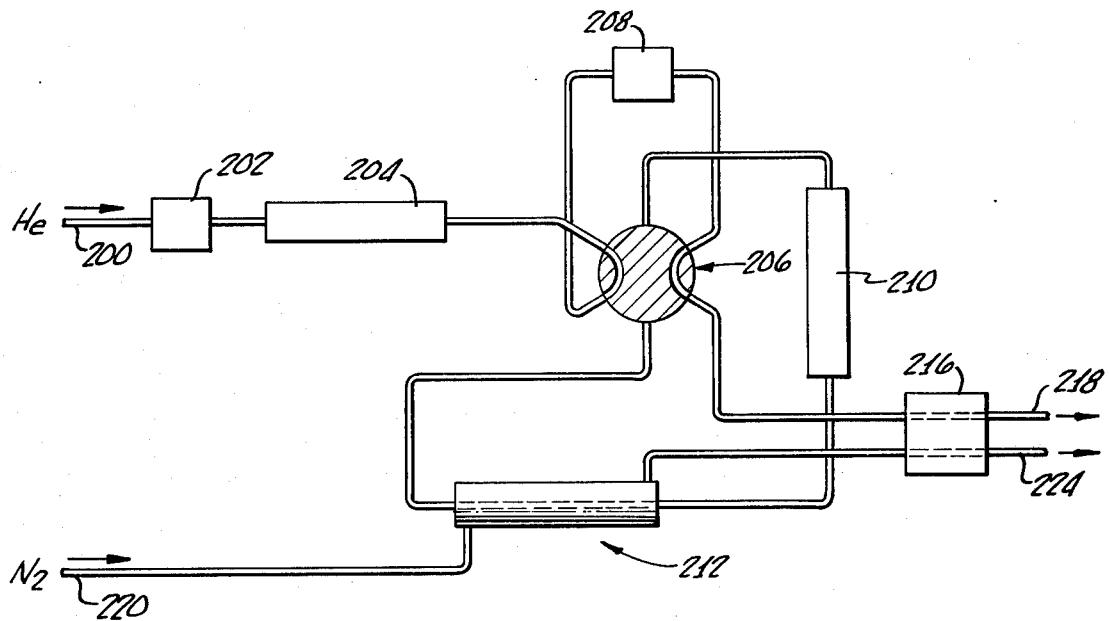

FIGS. 4A and 4B show a typical chromatographic system using the invention, in two modes of operation.

In FIG. 4A, the first carrier gas, helium, flows from a source indicated at 200 through a sample inlet 202, a column 204, one leg of switching valve 206, column 210 and through the palladium transfer tube 214 of the hydrogen transfer system 212, then through another leg of switching valve 206 through detector 216 and is discharged at 218. In this mode, the sample constituents which pass through the first and second columns 204 and 210 reach the transfer tube 214. Nitrogen, or other low thermal conductivity gas, is obtained from a source 220 and flows through the outer chamber 222 of hydrogen transfer unit 212 where it picks up hydrogen passing through the walls of transfer tube 214 and carries the hydrogen to detector 216 and is vented at 224.

With the switching valve in the second position shown in FIG. 4B, the helium flows through the inlet 202, column 204 and then through restrictor 208 and a leg of valve 206 directly to the detector 216 and to vent 218 without passing through the second column 210 or the hydrogen transfer system 212.

The system illustrated in FIGS. 4A and 4B is merely exemplary of essentially an unlimited number of chromatographic column and switching arrangements which can utilize the invention described in this patent. In general, any multiple column or other chromatographic system can utilize this invention when hydrogen is one of the components to be determined.

It will be apparent that the hydrogen transfer system is generally in the carrier gas system following the chromatographic column(s), in order that the hydrogen constituent be separated from other sample constituents at the time the hydrogen comes into contact with the hot palladium diffusion membrane. This is generally desirable to preclude reaction between the sample constituents, such as might occur, for example, between hydrogen and oxygen. It will be equally apparent that the hydrogen transfer system can be placed before or between chromatographic columns if the sample is such that no reaction will occur. For example, the system shown in FIG. 1 could be rearranged simply by exchanging the relative positions of the column 14 and the hydrogen transfer system 16.

Figure 6:
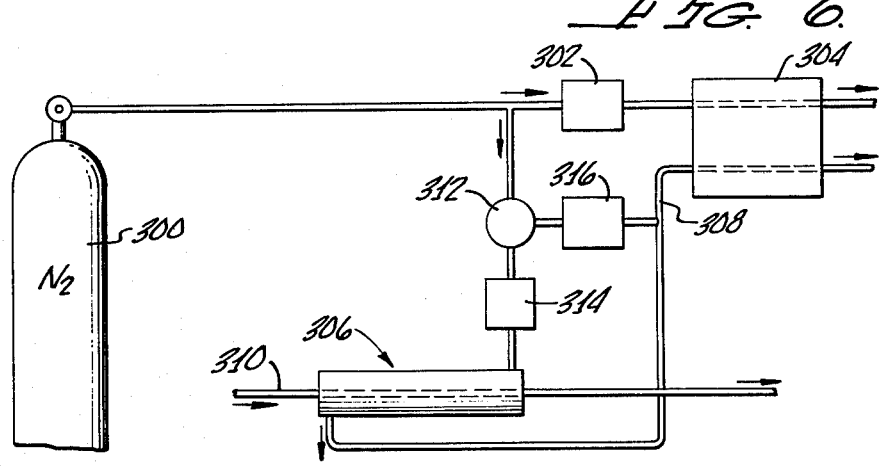
FIG. 6 is an alternative gas analysis system using the concept of this invention.

Hydrogen in a gas stream can also be monitored without the aid of chromatographic columns. A system for monitoring hydrogen in a gas stream, for example a process gas stream which contains hydrogen as one constituent, is illustrated in FIG. 6. The carrier gas for this analytical system is nitrogen or an equivalent low thermal conductivity gas from a source 300 which flows through a restrictor 302, if necessary to provide balanced gas flow, and a detector 304 of the type previously described. A second stream of nitrogen flows through a hydrogen transfer system 306 and through a second input 308 to the detector 304. The process gas or other gas stream flows through the interior tube 310, which includes the hydrogen permeable barrier membrane as previously described. In operation, the hydrogen will migrate through the hydrogen permeable barrier into the nitrogen carrier gas stream and is detected in the manner described. The zero level for hydrogen can be obtained by means of a selector valve 312 which permits pure nitrogen to be fed to both sides of the detector. Restrictors 314 and 316 permit setting the same flow through either path. This system provides for a continous monitor of the level of hydrogen in the gas stream to be sampled. An alternative approach is to flow a carrier gas through line 310 continuously and inject discrete samples of the process gas into the continuous stream from a process stream or other source as desired, either automatically or manually.

As indicated hereinbefore, certain terms are used in a shorthand sense. For example, reference is made to a palladium diffusion member as a shorthand for any material which is selectively permeable only to hydrogen, reference to helium as a first carrier gas and to nitrogen as a second carrier gas is merely a shorthand designation of a high thermal conductivity carrier gas in the first carrier gas system and a relatively lower thermal conductivity gas, such as nitrogen, argon, etc., in the second carrier gas system. Thermistors are referred to as an exemplary thermal conductivity sensing element, and the term will include other thermal conductivity sensing elements such as, for example, the heated filament type of sensing element. The term "process" stream refers to any fluid stream which includes the constituent to be determined, including streams into which a sample containing the constituent of interest is injected.

The foregoing illustrations, diagrams and discussions are directed to the preferred embodiments of the invention and the best means and method presently known to the inventor for carrying out the invention and is not a comprehensive disclosure of all possible configurations, systems or techniques which may embody or utilize the invention. Accordingly, many variations in configuration, technique and operation are possible within the scope of the invention as defined in the following claims.

What is claimed is:

1. A gas chromatograph for quantitatively determining hydrogen gas, comprising:
    a helium carrier gas system;
    a nitrogen carrier gas system;
    means for injecting a sample which includes hydrogen gas as a sample constituent into the helium carrier gas system;
    a chromatographic column in the helium carrier gas system for separating the sample into constituents;
    means for transferring the hydrogen constituent of the sample from the helium carrier gas system to the nitrogen carrier gas system without transferring other sample constituents, said nitrogen carrier gas flowing countercurrently to the helium carrier gas in said means for transferring the hydrogen;
    means in the helium carrier gas system for detecting sample constituents other than hydrogen; and
    means in the nitrogen carrier gas system for detecting the hydrogen constituent of the sample.

2. A gas chromatographic system for quantitatively determining the hydrogen gas constituent of a sample with high sensitivity, comprising:
    a first carrier gas system which includes means for conducting a first carrier gas from a gas source to an effluent port, means for injecting a hydrogen containing sample into the first carrier gas stream, a chromatographic column for separating hydrogen from other constituents of the sample in the first carrier gas stream, hydrogen transfer means for selectively transferring hydrogen from the first carrier gas stream through a barrier which is selectively permeable to hydrogen, the first carrier gas sweeping a first side of the barrier, and means for detecting sample constituents in the first carrier gas;

a second carrier gas system which includes means for conducting a second carrier gas in which hydrogen can be detected with greater sensitivity than in the first carrier gas from a gas source to a port, the second carrier gas stream sweeping the other side of the hydrogen permeable barrier in a countercurrent direction to receive hydrogen transferred from the first carrier gas stream, and means for detecting hydrogen in the second carrier gas stream.

3. In a gas chromatograph which includes a first carrier gas system, sample injection means, a chromatographic column, and a detector, the improvement comprising means in the first carrier gas system for selectively transferring hydrogen to a second carrier gas of higher molecular weight and wherein the detector is balanced to quantitatively determine hydrogen in the second carrier gas and other sample constituents in the first carrier gas, said second carrier gas system flowing in a direction counter to the direction of flow of the first carrier gas system.

4. The improved chromatograph defined in claim 3 wherein the hydrogen transfer means comprises a palladium conduit through which the first carrier gas flows surrounded by a second conduit through which the second carrier gas flows, the hydrogen permeating the palladium conduit and being carried to the detector by the second carrier gas.

5. The improved chromatograph defined in claim 4 wherein detector is balanced to detect hydrogen in nitrogen and other constituents in helium.

6. A process for quantitatively determining hydrogen comprising:
injecting a sample containing the hydrogen to be determined into a first chromatographic carrier gas stream;
chromatographically separating the hydrogen from other sample constituents;
passing the hydrogen selectively through a hydrogen permeable barrier into a countercurrently flowing second carrier gas stream in which hydrogen can be determined with greater sensitivity than in the first carrier gas; and
detecting hydrogen quantitatively in the second carrier gas.

7. The process defined in claim 6 wherein the other sample constituents are quantitatively determined in the first carrier gas.

8. The process defined in claim 6 wherein the first carrier gas is helium and the second carrier gas is an inert gas having substantially lower thermal conductivity than helium and wherein the hydrogen is detected by differential thermal conductivity.

9. The process defined in claim 8 wherein other sample constituents are determined in the helium carrier gas.

10. A process for quantitatively determining hydrogen comprising:
injecting a sample which contains hydrogen and other constituents into a helium carrier gas stream;
chromatographically separating hydrogen from other sample constituents;
passing the carrier gas which selectively contains hydrogen into contact with a palladium-silver membrane which is selectively permeable to hydrogen at a temperature of from about 400° C to about 650° C for thereby passing hydrogen selectively through said barrier into a counter currently flowing nitrogen or argon carrier gas stream;
detecting hydrogen quantitatively in the nitrogen or argon carrier gas steam.

* * * * *